United States Patent

Nearn et al.

[11] Patent Number: 5,417,961
[45] Date of Patent: May 23, 1995

[54] SUNSCREEN COMPOSITIONS

[75] Inventors: Malcolm R. Nearn, Kentlyn; Sandra J. Redshaw, Georges Hall; Graham Burgess, Bonnyrigg, all of Australia

[73] Assignee: Colgate-Palmolive Company, Piscataway, N.J.

[21] Appl. No.: 56,048

[22] Filed: Apr. 30, 1993

[51] Int. Cl.$^6$ .................. A61K 7/42; A61K 7/44; A61K 7/48; A61K 9/107
[52] U.S. Cl. ..................... 424/59; 424/60; 514/847; 514/937; 514/938; 514/969
[58] Field of Search ............ 424/59, 60; 514/938, 514/937

[56] References Cited

U.S. PATENT DOCUMENTS

| | | |
|---|---|---|
| 1,779,891 | 10/1930 | Risler ........................ 424/59 |
| 1,818,699 | 8/1931 | Dusenbury et al. ........... 424/59 |
| 2,175,213 | 10/1939 | Parson ....................... 424/59 |
| 2,267,200 | 12/1941 | Hersberger et al. .......... 424/59 |
| 2,435,005 | 1/1948 | Huppke et al. .............. 424/59 |
| 2,826,169 | 3/1958 | Le Veen .................... 424/59 X |
| 3,004,896 | 11/1961 | Heller et al. ............... 424/59 |
| 4,563,346 | 1/1986 | Deckner .................... 424/59 |
| 4,663,157 | 5/1987 | Brock ....................... 424/59 |
| 4,671,955 | 6/1987 | Palinczar ................... 424/59 |
| 4,671,956 | 6/1987 | Bouillon .................... 424/59 |
| 4,683,134 | 7/1987 | Palinezar ................... 424/59 |
| 4,699,779 | 10/1987 | Palinczar ................... 424/59 |
| 4,710,371 | 12/1987 | Palinczar ................... 424/59 |
| 4,731,242 | 3/1988 | Palinczar ................... 424/59 |
| 4,857,304 | 8/1989 | Ishiwatari et al. ........... 424/59 |
| 4,917,882 | 4/1990 | Strobridge ................. 424/59 |
| 5,032,390 | 7/1991 | Iwaya et al. ............... 424/59 |
| 5,093,109 | 3/1992 | Mausner .................... 424/59 |

FOREIGN PATENT DOCUMENTS

| | | | |
|---|---|---|---|
| 108036 | 9/1974 | German Dem. Rep. ........ | 424/59 |
| 113168 | 5/1975 | German Dem. Rep. ........ | 424/59 |
| 2533497 | 2/1977 | Germany ................... | 424/59 |

OTHER PUBLICATIONS

Chemical Abstracts 86:145800, Creams for Protection Against Radiation, Light and the Sun, German Offen. 2533497, 1977.

*Primary Examiner*—Dale R. Ore
*Attorney, Agent, or Firm*—Martin B. Barancik; Robert C. Sullivan

[57] ABSTRACT

A sunscreen composition comprising a water-in-oil emulsion which comprises an aqueous phase and an oil phase, the oil phase comprising an organic sunscreen agent and polyethylene, the oil phase having suspended therein microfine zinc oxide having a particle size in the range of from about 0.01 to about 0.25 microns, the amount of sunscreen agent being in the range of from about 1% to about 12%, the amount of polyethylene being in the range of from about 0.2% to about 5% and the amount of zinc oxide being in the range of from about 1% to about 10%, the percentages being by weight based on the weight of the water-in-oil emulsion.

9 Claims, No Drawings

SUNSCREEN COMPOSITIONS

BACKGROUND OF THE INVENTION

1. Field of the Invention

The present invention relates to novel sunscreen compositions.

2. Description of the Prior Art

Sunscreen compositions are commonly used during outdoor work or leisure pursuits for protection of exposed skin against painful sunburn. Many effective sunscreen preparations are sold commercially or are described in the cosmetic or pharmaceutical literature. In general, sunscreen preparations are formulated in the form of a cream, lotion or oil containing as the active agent an ultraviolet radiation-absorbing chemical compound. The active agent acts to block the passage of erythematogenic radiation, thereby preventing its penetration into the skin.

The ideal sunscreen formulation should be nontoxic and non-irritating to skin tissue and be capable of convenient application to the skin in a uniform and continuous film. The product should be sufficiently stable chemically and physically so as to provide an acceptable shelf life upon storage. It is particularly desirable that the preparation should retain its protective effect over a prolonged period after application. Thus, the active agent when present on the skin must be resistant to chemical- or photo-degradation, to absorption through the skin and to removal by perspiration, skin oil or water. For aesthetic reasons, the product should be substantially odorless (or be capable of being scented) and be non-staining to the skin or clothing.

Many agents have been found to be effective sunscreen agents. Among the effective sunscreen agents heretofore employed are certain cinnamate esters, in particular, octyl methoxycinnamate. See, for example, U.S. Pat. Nos. 4,917,882; 5,093,109; 4,671,955 and 4,683,134.

Finely divided zinc oxide (ZnO) has also been employed as a sunscreen agent. See U.S. Patent 5,032,390 and PCT International Publication WO 92/13517. It has been suggested to combine ZnO and cinnamate esters in sunscreen compositions. See U.S. Pat. Nos. 4,917,882; 4,671,955 and 4,683,134.

U.S. Pat. No. 4,264,581 describes a sunscreen composition containing the sunscreen agents octyl dimethyl p-aminobenzoic acid ester and oxybenzone in combination with a small amount of polyethylene. The specific function of the polyethylene in the composition is not disclosed.

It is an object of the present invention to provide a novel sunscreen composition.

SUMMARY OF THE INVENTION

The above and other objects are realized by the present invention, one embodiment of which relates to a sunscreen composition comprising a water-in-oil emulsion which comprises an aqueous phase and an oil phase, the oil phase comprising an organic UV-absorbing sunscreen agent such as, e.g., octyl methoxycinnamate, octyl dimethyl para-aminobenzoic acid, octocrylene (2-ethylhexyl-2-cyano-3,3-diphenylacrylate) and mixtures thereof, and polyethylene, the oil phase having suspended therein microfine zinc oxide having a particle size in the range of from about 0.01 to about 0.25 microns, the amount of octyl methoxycinnamate being in the range of from about 1% to about 12%, the amount of polyethylene being in the range of from about 0.2% to about 5% and the amount of zinc oxide being in the range of from about 1% to about 10%, the percentages being by weight based on the weight of the water-in-oil emulsion.

DETAILED DESCRIPTION OF THE INVENTION

The present invention is predicated on the discovery that the addition of polyethylene in specific critical amounts to a water-in-oil emulsion containing the sunscreen agents ZnO having a specific particle size and the above sunscreen agents synergistically enhances the sun protection factor of the combined sunscreen agents.

Thus, it is expected that the contribution of individual sunscreen agents to the overall sun protection factor (SPF) of a composition containing the agents is additive. Unexpectedly, however, it has been found that the presence of polyethylene in sunscreen compositions containing ZnO and the above sunscreen agents synergistically increases the SPF of the composition to a value far greater than the sum of the SPF's of the individual sunscreen agents.

It is preferred that the sunscreen composition be formulated in water-in-oil emulsion form, and most preferably in the form of a cream or lotion.

The ZnO, sunscreen agent and polyethylene are preferably dissolved or suspended in an oil phase and the aqueous phase added thereto under strong homogenization to produce the water-in-oil emulsion. The weight ratio of the aqueous phase to the oil phase in the emulsion compositions of the invention is preferably in the range of from about 2:1 to about 1:4.

The amount of sunscreen agent may vary from about 1% to about 12%, and most preferably from about 4% to about 10%.

The amount of polyethylene incorporated into the water-in-oil emulsion composition of the invention should be in the range of from about 0.2% to about 5%, and most preferably from about 0.5% to about 3%.

Suitable ingredients for forming the oil phase include:
Light liquid paraffin (emollient)
Liquid paraffin (emollient)
C12-15 alkyl benzoate (emollient)
Fatty acid esters, e.g., isopropyl palmitate, cetearyl octanoate (emollient)
Triglycerides (emollient)
Lecithin (dispersant for ZnO)
Glyceryl sorbitan oleostearate (emulsifier)
PEG-7 hydrogenated castor oil (emulsifier)
Silicone oil (provides water resistance)
PVP hexadecene copolymer (provides water resistance)
Polyethylene (aids film formation)
Solulan PB20 (dispersant for ZnO)
Cyclomethicone (skin feel)

It will be understood by those skilled in the art that any inert cosmetically acceptable oil which is capable of suspending particulate ZnO and dissolving the sunscreen agent and when hot of dissolving the polyethylene may be utilized in the compositions of the invention.

It will also be understood that any conventional adjuvant, including emulsifying agent, stabilizer, preservative, etc., conventionally employed in water-in-oil sunscreen compositions may be added to either or both of the phases of the composition of the invention.

Exemplary of suitable adjuvants are:

Light liquid paraffin (emollient)
Liquid paraffin (emollient)
C12-15 alkyl benzoate (emollient)
Fatty acid esters, e.g., isopropyl palmitate, cetearyl octanoate (emollient)
Triglycerides (emollient)
Lecithin (dispersant for ZnO)
Glyceryl sorbitan oleostearate (emulsifier)
PEG-7 hydrogenated castor oil (emulsifier)
Silicone oil (provides water resistance)
PVP hexadecene copolymer (provides water resistance)
Polyethylene (aids film formation)
Solulan PB20 (dispersant for ZnO)
Imidazolidinyl urea (preservative)
Phenonip (preservative)
Parabens (preservative)
BHT (anti-oxidant)
Propylene glycol (moisturizer)
Magnesium sulfate (emulsion stabilizer)
Cyclomethicone (skin feel)

The invention is illustrated by the following non-limiting examples.

EXAMPLE 1

The ingredients in the compositions listed in Table I were formulated as follows:

A zinc oxide premix was prepared by blending ZnO having a particle size of 0.1 μm, light liquid paraffin, PVP/hexadecene copolymer, PPG-20 lanolin alcohol ether, lecithin and cetearyl octanoate, followed by passing the blend through a triple roll mill.

An oil phase was prepared by heating polyethylene in isopropyl palmitate at 120° C. until dissolved, followed by adding the remainder of the oil phase ingredients, e.g., light liquid paraffin, C12-15 alkyl benzoate, isopropyl palmitate, phenyl trimethicone, glyceryl sorbitan oleostearate and PEG-7 hydrogenated castor oil, including the octyl methoxycinnamate and the zinc oxide premix which were preheated to 80° C. Strong shear was applied to the mix in a homogenizer until the oil phase was uniform.

The aqueous phase was prepared by adding the water-soluble components, e.g., propylene glycol and magnesium sulfate, to water with mixing at 80° C.

The aqueous phase is then added to the oil phase with strong homogenization until a uniform water-in-oil emulsion is obtained which is then cooled to about 40°–45° C. Cyclomethicone and preservatives (and fragrances, if needed) are then added and the emulsion further cooled to room temperature.

TABLE I

| Ingredients | I | II | III | IV | V | VI | VII |
|---|---|---|---|---|---|---|---|
| Proplyene Glycol | 2.0 | 2.0 | 2.0 | 2.0 | 2.0 | 2.0 | 2.0 |
| Magnesium Sutfate | 0.5 | 0.5 | 0.5 | 0.5 | 0.5 | 0.5 | 0.5 |
| Germall 115 (imidazolidinyl urea) | 0.2 | 0.2 | 0.2 | 0.2 | 0.2 | 0.2 | 0.2 |
| Methylparaben | 0.15 | 0.15 | 0.15 | 0.15 | 0.15 | 0.15 | 0.15 |
| Water | 50.37 | 50.37 | 50.37 | 50.37 | 50.60 | 50.60 | 54.35 |
| Arlacel 481 (glyceryl sorbitan oleostearate) | 1.5 | 1.5 | 1.5 | 1.5 | 1.5 | 1.5 | 1.5 |
| Arlacel 989 (PEG-7 hydrogemted castor oil) | 6.0 | 6.0 | 6.0 | 6.0 | 6.0 | 6.0 | 6.0 |
| Light Liquid Paraffin | 5.0 | 5.0 | 5.0 | 5.0 | 5.0 | 5.0 | 5.0 |
| Silicone 556 (phenyl trimethicone) | 2.0 | 2.0 | 2.0 | 2.0 | 2.0 | 2.0 | 2.0 |
| ZnO Paste * | 7.23 | 7.23 | 7.23 | 7.23 | — | — | — |
| Finsolv TN (C12-15 alkyl benzoate) | 1.0 | 1.0 | 1.0 | 1.0 | 1.0 | 1.0 | 1.0 |
| Propylparaben | 0.05 | 0.05 | 0.05 | 0.05 | 0.05 | 0.05 | 0.05 |
| Parsol MCX (octyl methoxycinnamate) | — | — | 5.0 | 5.0 | 5.0 | 5.0 | — |
| (Polyethylene 617 (polyethylene) | — | 2.0 | — | 2.0 | 2.0 | — | 1.25 |
| Isopropyl Palmitate | 21.0 | 19.0 | 16.0 | 14.0 | 21.0 | 23.0 | 23.0 |
| Silicone 344 (cyclomethicone) | 3.0 | 3.0 | 3.0 | 3.0 | 3.0 | 3.0 | 3.0 |
| TOTAL | 100.0 | 100.0 | 100.0 | 100.0 | 100.0 | 100.0 | 100.0 |
| Sun Protection Factor (SPF) | 4.7 | 4.6 | 17.6 | 31.7 | 9.7 | 5.9 | 1.3 |

* Zinc Oxide (ZnO) Paste

| | |
|---|---|
| Finex Zinc oxide | 5.0 |
| Light Liquid Paraffin | 1.5 |
| Antaron V216 (PVP/hexadecene copolymer) | 0.06 |
| Solulan P820 (PPG-20 lanolin alcohol ether) | 0.175 |
| Lecithin | 0.12 |
| PCL Liquid (cetearyl octanoate) | 0.375 |
| | 7.23 |

The sun protection factor (SPF) for each formulation was determined by the method described in the Australian Standard AS 2604-1986, "Sunscreen Products—Evaluation and Classification" (Standards Association of Australia, 1986).

The SPF's of the various formulations are set forth in Table II for comparison purposes.

TABLE II

| Formulation | % Octyl Methoxy-cinnamate | % Poly-ethylene | % ZnO | SPF |
|---|---|---|---|---|
| I | — | — | 5 | 4.7 |
| II | — | 2 | 5 | 4.6 |
| III | 5 | — | 5 | 17.6 |
| IV | 5 | 2 | 5 | 31.7 |
| V | 5 | 2 | — | 9.7 |
| VI | 5 | — | — | 5.9 |
| VII | — | 1.25 | — | 1.3 |

The synergistic effect of the polyethylene on the SPF of the octyl methoxycinnamate and ZnO components of the composition is apparent from the data set forth in Table II. It would be expected that the SPF of Formulation IV (containing 2% polyethylene, 5% ZnO and 5% octyl methoxycinnamate) would be the sum of the SPF's of Formulation V (containing 2% polyethylene and 5% octyl methoxycinnamate) and Formulation II (containing 2% polyethylene and 5% ZnO), i.e., 4.6+9.7=14.3. However, the actual measured SPF of Formulation IV is 31.7; more than twice the expected value. It should be further noted that the SPF value for polyethylene alone is only 1.3, thereby evidencing that it has little, if any, intrinsic sun protection properties, but that it does contribute synergistically to compositions containing organic sunscreen agents and ZnO of the requisite particle size.

EXAMPLE 2

The procedure of Example 1 was repeated to prepare formulations containing the ingredients set forth in Table III below.

TABEL III

| Formulation | % Octyl Methoxycinnamate | % Polyethylene | % Microfine Zinc Oxide Z-Cote[a] | % Microfine Zinc Oxide Microsol Z[b] | SPF |
|---|---|---|---|---|---|
| A | — | 2.0 | 5.0 | — | 3.7 |
| B | 5.0 | 2.0 | 5.0 | — | 33.1 |
| C | — | — | 5.0 | — | 3.8 |
| D | — | 2.0 | — | 5.0 | 3.0 |
| E | 5.0 | 2.0 | — | 5.0 | 34.3 |
| F | — | — | — | 5.0 | 3.7 |

[a]SunSmart, Inc., New York
[b]Micronisers Pty. Ltd., Australia

Similarly to the results set forth in Table II, the synergistic effect of the polyethylene on the SPF of the octyl methoxycinnamate and ZnO components of the compositions is apparent from the data set forth in Table III. The SPF values for Formulations B (33.1) and E (34.3) are much more than the expected values.

EXAMPLE 3

The procedure of Example 1 was repeated to prepare the formulations set forth in Table IV below.

TABLE IV

| Formulation | % Polyethylene | % Zno | % Octyl Methoxycinnamate | % Padimate O[a] | % Octocrylene | SPF |
|---|---|---|---|---|---|---|
| 1 | 2 | — | — | 5.0 | — | 12.7 |
| 2 | 2 | 5.0 | — | 5.0 | — | 27.0 |
| 3 | 2 | — | — | — | 5.0 | 7.9 |
| 4 | 2 | 5.0 | — | — | 5.0 | 16.2 |
| 5 | 2 | — | 5.0 | — | — | 9.6 |
| 6 | 2 | 5.0 | 5.0 | — | — | 31.7 |

[a]Octyl dimethyl PABA

Again the SPF values for Formulations 2, 4 and 6 are significantly higher than expected.

EXAMPLE 4

The procedure of Example 1 was repeated to prepare the formulations containing the ingredients set forth in Table V below.

TABLE V

| % Microfine Zinc Oxide | % Microfine Titanium Dioxide | % Polyethylene | SPF |
|---|---|---|---|
| 5 | — | — | 4.7 |
| 5 | 2 | — | 4.6 |
| — | 5 | — | 10.0 |
| — | 5 | 2 | 23.0 |
| 5 | 5 | 2 | 26.0 |
| 5 | 5 | — | 21.0 |

As apparent from the results set forth in Table V, there is no synergy in the system containing microfine titanium dioxide and zinc oxide and polyethylene.

It will be understood by those skilled in the art that the water-in-oil emulsion compositions of the invention may be formulated in cream, lotion, ointment or other form.

Creams may be prepared, e.g., by employing different proportions of Arlacel 481 and Arlacel 989 in the example. Thus, if Arlacel 481 (5%) and Arlacel 989 (2%) are employed in Example 1, the resultant products are creams.

The products produced by the method of Example 1 are lotions.

We claim:

1. A sunscreen composition comprising a water-in-oil emulsion which comprises an aqueous phase and an oil phase, said oil phase comprising polyethylene and an UV-absorbing organic sunscreen agent, said oil phase having suspended therein microfine zinc oxide having a particle size in the range of from about 0.01 to about 0.25 microns, the amount of sunscreen agent being in the range of from about 1% to about 12%, the amount of polyethylene being in the range of from about 0.2% to about 5% and the amount of zinc oxide being in the range of from about 1% to about 10%, said percentages being by weight based on the weight of said water-in-oil emulsion.

2. The sunscreen composition of claim 1 wherein said sunscreen agent is selected from the group consisting of octyl methoxycinnamate, octyl dimethyl PABA, octocrylene and mixtures thereof.

3. The sunscreen composition of claim 1 wherein the weight ratio of said aqueous phase to said oil phase is in the range of from about 2:1 to about 1:5.

4. The sunscreen composition of claim 1 wherein said water-in-oil emulsion comprises a cream.

5. The sunscreen composition of claim 1 wherein said water-in-oil emulsion comprises a lotion.

6. The sunscreen composition of claim 1 wherein said water-in-oil emulsion comprises an ointment.

7. The sunscreen composition of claim 1 wherein said sunscreen agent is octyl methoxycinnamate.

8. The sunscreen composition of claim 1 wherein said sunscreen agent is octyl dimethyl PABA.

9. The sunscreen composition of claim 1 wherein said sunscreen agent is octocrylene.

* * * * *